(12) United States Patent
Williams et al.

(10) Patent No.: US 6,776,157 B2
(45) Date of Patent: Aug. 17, 2004

(54) MEDICAL PACIFIER AND METHOD FOR USE THEREOF

(75) Inventors: Kayode A. Williams, Ann Arbor, MI (US); John H. Huntington, Orland Park, IL (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/808,512

(22) Filed: Mar. 14, 2001

(65) Prior Publication Data

US 2002/0129816 A1 Sep. 19, 2002

(51) Int. Cl.[7] .......................... A61M 16/00; A61J 17/00
(52) U.S. Cl. .......................... 128/203.12; 128/204.18; 128/200.26; 606/234; 606/236
(58) Field of Search ................... 606/234, 235, 606/236; 128/207.14, 200.26, 204.17, 202.27, 911, 204.18, 203.12, 201.26, 206.29, 203.29

(56) References Cited

U.S. PATENT DOCUMENTS

| | | | | |
|---|---|---|---|---|
| 1,592,345 A | * | 7/1926 | Drager | 128/207.17 |
| 2,693,182 A | * | 11/1954 | Phillips | 128/200.26 |
| 3,669,112 A | * | 6/1972 | Mager et al. | 215/11.1 |
| 4,132,232 A | * | 1/1979 | Lerner | 606/236 |
| 4,520,809 A | | 6/1985 | de Greef et al. | |
| 4,637,388 A | * | 1/1987 | Melendy | 128/207.14 |
| 4,790,327 A | * | 12/1988 | Despotis | 600/532 |
| 4,896,666 A | | 1/1990 | Hinkle | |
| 4,953,548 A | * | 9/1990 | Stoddard et al. | 128/207.14 |
| 4,994,076 A | * | 2/1991 | Guss | 215/11.1 |
| 5,078,734 A | | 1/1992 | Noble | |
| 5,121,746 A | * | 6/1992 | Sikora | 128/203.12 |
| 5,146,913 A | * | 9/1992 | Khorsandian et al. | 128/200.26 |
| 5,176,705 A | | 1/1993 | Noble | |
| 5,375,593 A | | 12/1994 | Press | |
| 5,392,774 A | * | 2/1995 | Sato | 128/207.15 |
| 5,462,050 A | | 10/1995 | Dahlstrand | |
| 5,512,047 A | * | 4/1996 | Dvorak | 604/77 |
| 5,514,142 A | | 5/1996 | Dean-Homolka | |
| 5,542,415 A | * | 8/1996 | Brody | 128/204.21 |
| 5,640,951 A | * | 6/1997 | Huddart et al. | 128/204.17 |
| 5,685,291 A | * | 11/1997 | Marsh | 128/200.15 |
| 5,765,558 A | * | 6/1998 | Psaros et al. | 128/207.14 |
| 5,772,685 A | * | 6/1998 | Crowe et al. | 604/73 |
| 5,810,000 A | | 9/1998 | Stevens | |
| 5,823,184 A | * | 10/1998 | Gross | 128/204.18 |
| 5,830,235 A | | 11/1998 | Standley | |
| 5,868,131 A | * | 2/1999 | Murchie | 128/202.13 |
| 5,891,165 A | | 4/1999 | Buckner | |
| 5,904,140 A | | 5/1999 | McGoogan | |
| 6,003,511 A | * | 12/1999 | Fukunaga et al. | 128/202.27 |
| 6,110,193 A | * | 8/2000 | Chen | 604/77 |
| 6,120,528 A | * | 9/2000 | Link et al. | 128/847 |
| 6,125,847 A | * | 10/2000 | Lin | 128/204.17 |
| 6,197,044 B1 | * | 3/2001 | Clayton | 606/236 |
| 6,626,168 B1 | * | 9/2003 | Carroll et al. | 128/200.14 |
| 2004/0040556 A1 | * | 3/2004 | Fillyaw | |

OTHER PUBLICATIONS

K.A. Williams, et al., The Pacifier Airway Device—A Novel Approach to Pediatric Inhalational Induction of Anesthesia, Midwest Anesthesiology Residents' Conference (MARC) Abstract, Mar. 17, 2000.

* cited by examiner

*Primary Examiner*—Henry Bennett
*Assistant Examiner*—Mital Patel
(74) *Attorney, Agent, or Firm*—Brooks Kushman P.C.

(57) ABSTRACT

A medical pacifier for delivering anesthesia and other gases into the oral cavity of a patient, such as an infant or child, is provided. The pacifier includes a nipple member adapted to be received within an oral cavity of the patient, the nipple member having a conduit extending therethrough and an outlet opening provided therein. A base is attached to the nipple member and adapted to remain outside the oral cavity. The base includes an inlet opening provided therein and a lumen extending therethrough which is in fluid communication with the conduit of the nipple member. The inlet opening is adapted to be connected to an external gas source such that gas can flow through the base and the nipple member for delivery via the outlet opening into the oral cavity of the patient.

28 Claims, 3 Drawing Sheets

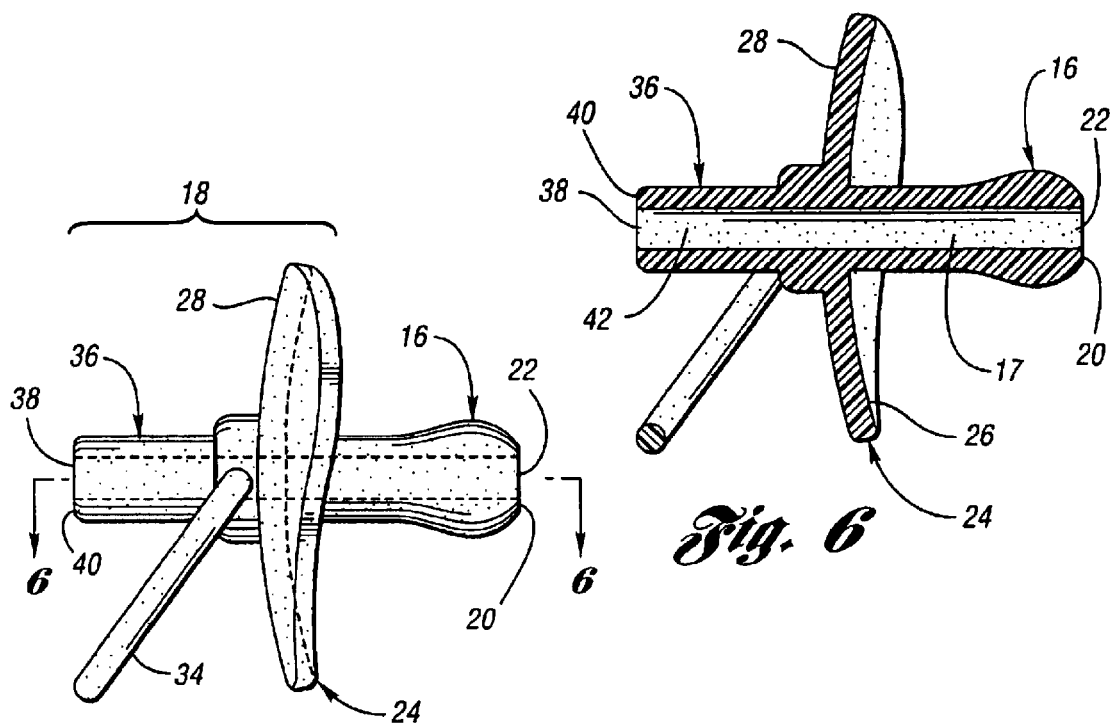
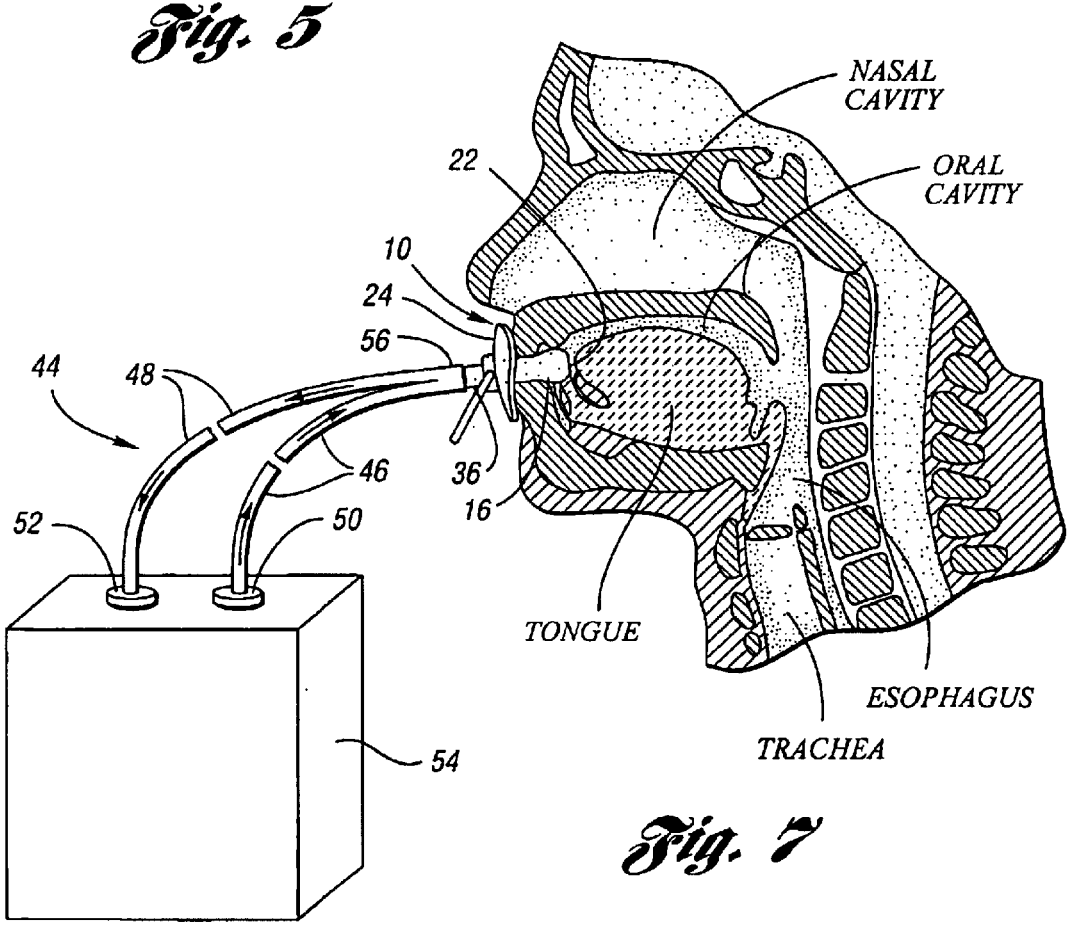

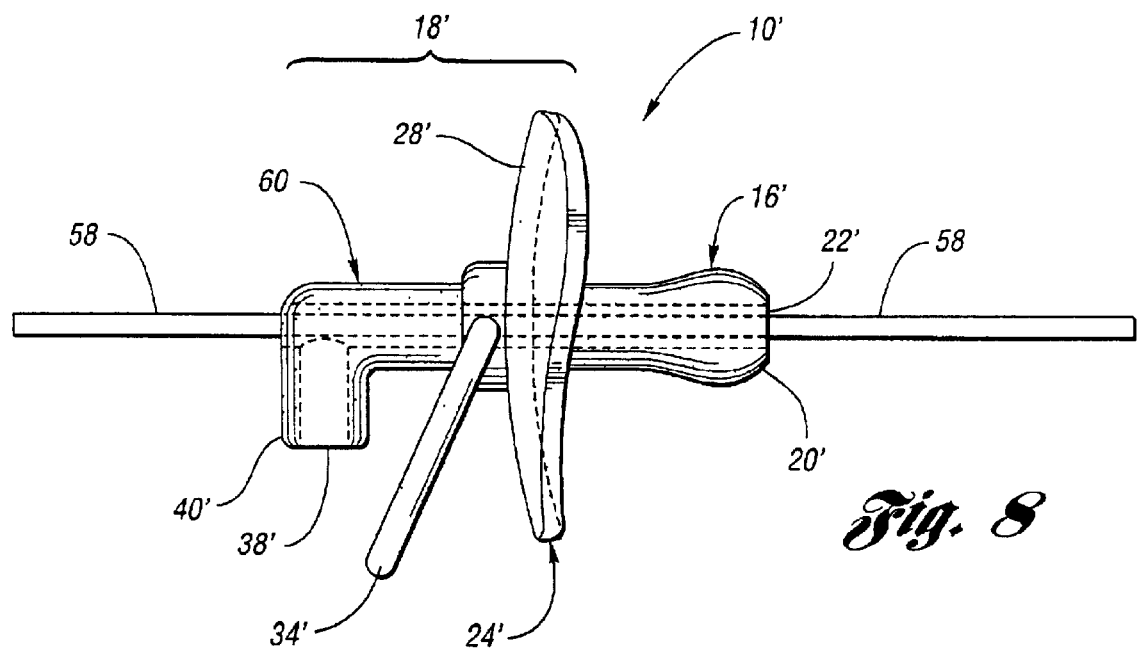
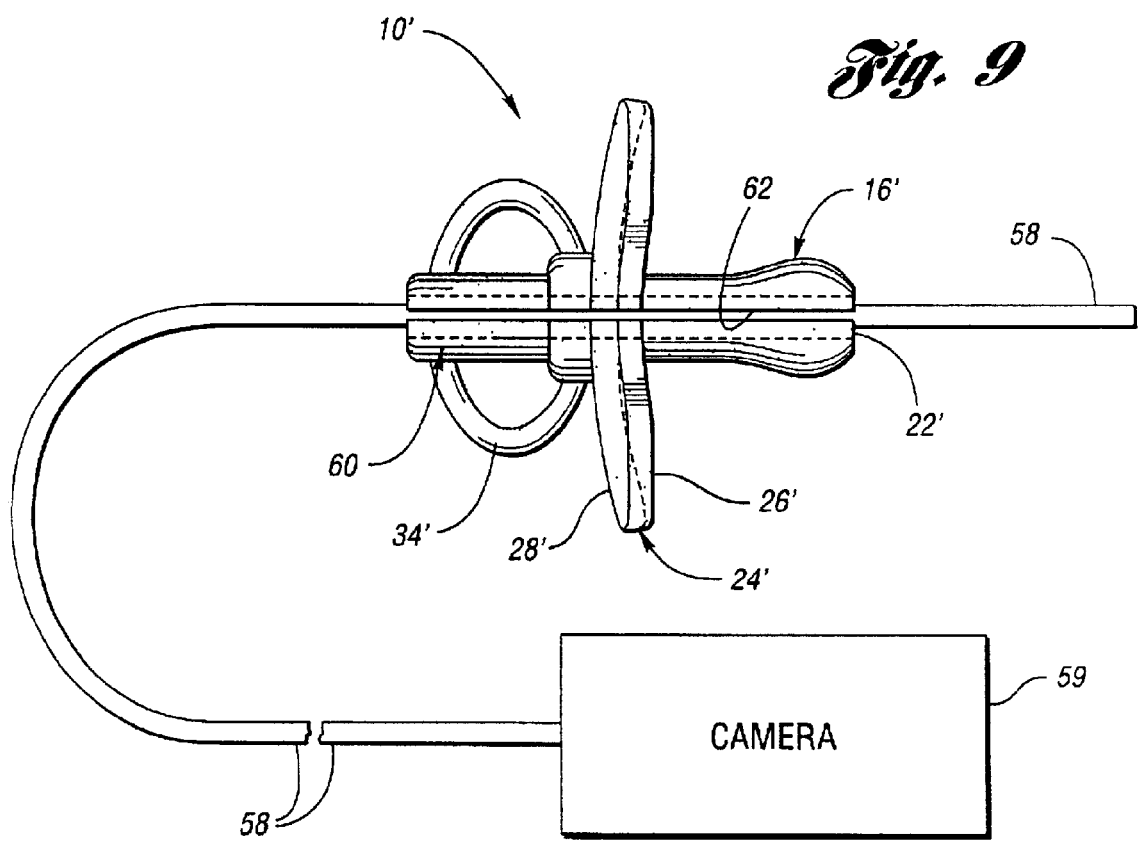

MEDICAL PACIFIER AND METHOD FOR USE THEREOF

BACKGROUND OF THE INVENTION

1. Field of the Invention

This invention relates to a medical pacifier and method for use thereof in providing anesthesia and other gases to pediatric patients.

2. Background Art

Induction of general anesthesia in infants and young children is most commonly accomplished by inhalation of anesthetic gases via the respiratory tract. In addition, the use of inhaled medications is often used for the treatment of pediatric patients with asthma and other illnesses.

For induction of anesthesia, the gas delivery system usually comprises a plastic or rubber face mask sized to cover a child's nose and mouth. Application of the face mask is unfamiliar and fear-inducing for the child, and most children to experience a smothering sensation. The resulting anxiety causes a child to struggle, hold his breath, and scream or cry. In addition, children also object to the smell of the anesthetic agent. Unfortunately, once the child is distressed, administration of anesthesia becomes much more difficult. Consequently, the infant or child usually requires preoperative sedative medicine to quiet him or her before the anesthesiologist is able to approach the child with the face mask.

Many children will suck vigorously at the edge of a standard face mask as the anesthesiologist attempts to cover the child's nose and mouth. While such suckling instinctively quiets and calms a child, it will often prevent the face mask from being properly positioned on the child's face. This, in turn, prevents a tight seal from being formed around of the edge of the mask, such that a significant amount of anesthetic gas may potentially leak from the mask and induction of anesthesia is slowed. Therefore, the mask must often be continuously pressed against the child's face by a medical practitioner in order to maintain sealed contact during administration of the anesthesia.

Due to a child's innate propensity to suckle, many pediatric anesthesiologists have resorted to giving a pacifier to the child prior to induction of anesthesia. In fact, children accustomed to a pacifier will often be anesthetized using a face mask secured over the child's nose and mouth with the pacifier in place. However, such a procedure usually requires the anesthesiologist to use a larger face mask, which increases the difficulty of maintaining a tight fit of the mask to the face. A larger mask size also increases the dead space inside the mask, which can lead to respiratory complications due to the inhalation of expired carbon dioxide.

Due to these difficulties, medical pacifiers have been developed which are capable of delivering anesthesia or other gases without use of a standard face mask. For example, U.S. Pat. No. 5,904,140 discloses a pacifier which includes a body having an inlet connected to a nebulizer for receiving air-entrained medication, and a closed end mounted to a stopper which carries a nipple. The body includes a discharge port over which a deflector is mounted. In operation, the air-entrained medication exits the pacifier body through the discharge port and is directed by the deflector toward the nostrils of an infant sucking on the nipple. As another example, U.S. Pat. No. 5,375,593 discloses a pacifier having a housing, a nipple connected to the housing, and a pair of nasal cannulae which extend out of the housing and are connected to an external oxygen source. The cannulae are positioned such that they are directed into the nostrils for discharging gas when the pacifier is placed in an infant's mouth.

While pacifiers such as those described above overcome some of the problems associated with standard anesthesia face masks, additional problems are introduced due to their method of operation. First, since the devices do not form a seal around the nostrils and merely direct anesthetic gas toward the nostrils, an unacceptable amount of anesthetic gas may be dispersed into the room air. Second, anesthesia and other gases inhaled via the nasal passages are naturally filtered, thereby reducing the amount of gas which reaches the lungs of the patient over a given time. This may result in a longer time required for inhalation therapy to be performed, and possibly less consistent and less efficacious outcomes.

SUMMARY OF THE INVENTION

Therefore, it is an object according to the present invention to provide a medical pacifier and method for use thereof which provide improved comfort and efficiency during induction of anesthesia and other gases.

It is a further object according to the present invention to provide a medical pacifier and method for use thereof wherein induction of anesthesia and other gases is accomplished via the oral cavity.

It is another object according to the present invention to provide a medical pacifier and method for use thereof which are readily accepted by pediatric patients.

It is still another object according to the present invention to provide a medical pacifier that is simple and inexpensive to manufacture.

Accordingly, a medical pacifier for delivering anesthesia and other gases into the oral cavity of a patient, such as an infant or child, is provided. The pacifier includes a nipple member adapted to be received within an oral cavity of the patient, the nipple member having a conduit extending therethrough and an outlet opening provided therein. A base is attached to the nipple member and adapted to remain outside the oral cavity. The base includes an inlet opening provided therein and a lumen extending therethrough which is in fluid communication with the conduit of the nipple member. The inlet opening is adapted to be connected to an external gas source such that gas can flow through the base and the nipple member for delivery via the outlet opening into the oral cavity of the patient.

The pacifier is preferably molded from a plastic material and is of one-piece construction. The base includes a base plate disposed generally perpendicular to a longitudinal axis of the nipple member, where the base plate includes a concave front surface facing the nipple member, and a convex rear surface facing away from the nipple member. The base further includes a connector projecting from the rear surface of the base plate, where the lumen extends through the connector and the inlet opening is disposed in a proximal end of the connector. Preferably, the outlet opening is provided in a distal end of the nipple member, and a handle ring is preferably pivotally attached to the rear surface of the base plate.

The proximal end of the connector preferably has an outer diameter of approximately 15 mm to provide compatible attachment to a standard external breathing tube. In one embodiment, the connector is generally L-shaped, and the pacifier includes a longitudinal slit formed therein for receiving an endoscope. In addition, the nipple member can be impregnated with medication to be dispensed to the patient.

In further accordance with the present invention, an apparatus for inducing anesthesia in patient is provided. The apparatus includes a breathing circuit including a source of anesthetic gas and an inlet tube connected to the source and operable to transport the gas toward the patient. The apparatus further includes a medical pacifier connected to the breathing circuit. The pacifier includes a nipple member adapted to be received within an oral cavity of the patient, the nipple member having a conduit extending therethrough and an outlet opening provided therein. A base is attached to the nipple member and adapted to remain outside the oral cavity. The base includes an inlet opening provided therein and a lumen extending therethrough which is in fluid communication with the conduit of the nipple member. The inlet opening is adapted to be connected to the inlet tube such that anesthetic gas can flow through the base and the nipple member for delivery via the outlet opening into the oral cavity of the patient.

Correspondingly, a method for delivering anesthesia or other gases to a patient is provided. The method includes inserting a medical pacifier into an oral cavity of the patient, the pacifier including a nipple member adapted to be received within the oral cavity and a base attached to the nipple member and adapted to remain outside the oral cavity. The nipple member includes a conduit extending therethrough and an outlet opening provided therein, and the base includes an inlet opening provided therein and a lumen extending therethrough which is in fluid communication with the conduit of the nipple member. The method further includes connecting a gas source to the inlet opening, and supplying gas through the base and the nipple member for delivery via the outlet opening into the oral cavity of the patient.

Gas is typically supplied by delivering gas toward the pacifier under positive pressure. The nipple member may be dipped into a dextrose solution prior to inserting the pacifier into the oral cavity of the patient, and medication may be dispensed into the oral cavity via the nipple member. For intubation procedures, the method may include inserting an endoscope through the pacifier and into the oral cavity of the patient. Lastly, the method can include placing a face mask on the patient for subsequent anesthetizing.

The above objects along with other objects, features, and advantages of the present invention are more readily understood from a review of the attached drawings and the accompanying specification and claims.

BRIEF DESCRIPTION OF THE DRAWINGS

FIG. 5 is a right side elevational view of the medical pacifier of FIG. 1;

FIG. 6 is a cross-sectional view of the medical pacifier taken along line 6—6 of FIG. 5;

FIG. 7 is a schematic representation of the medical pacifier of the present invention positioned within a child's mouth and connected to a standard anesthesia breathing circuit;

FIG. 8 is a right side elevational view of an alternative embodiment of the medical pacifier of the present invention which is adapted to receive an endoscope therein; and FIG. 9 is a top plan view of the medical pacifier of FIG. 9.

DETAILED DESCRIPTION OF THE PREFERRED EMBODIMENT(S)

Figure 1:
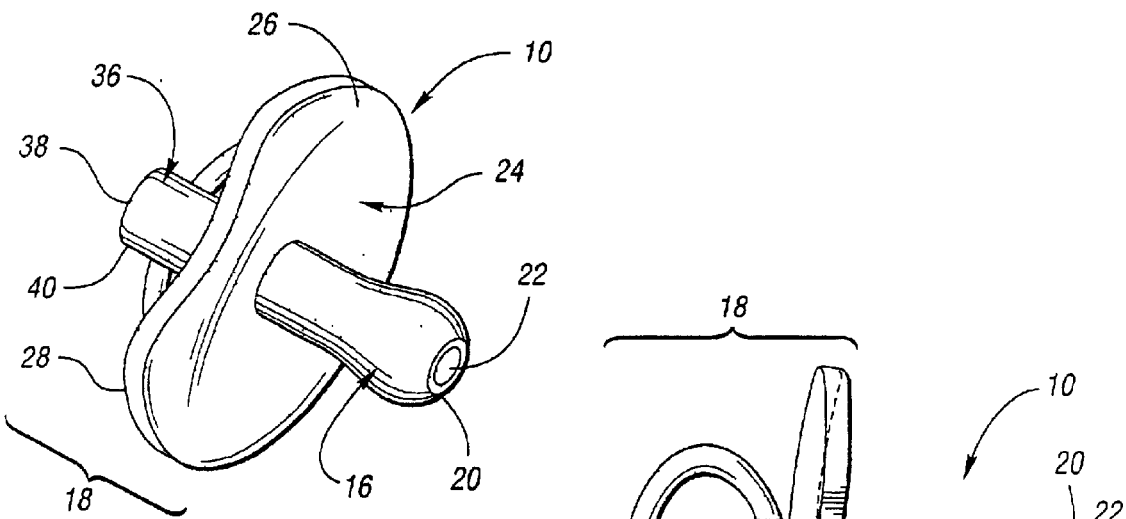
FIG. 1 is a perspective view of a medical pacifier constructed in accordance with the present invention.
Figure 2:
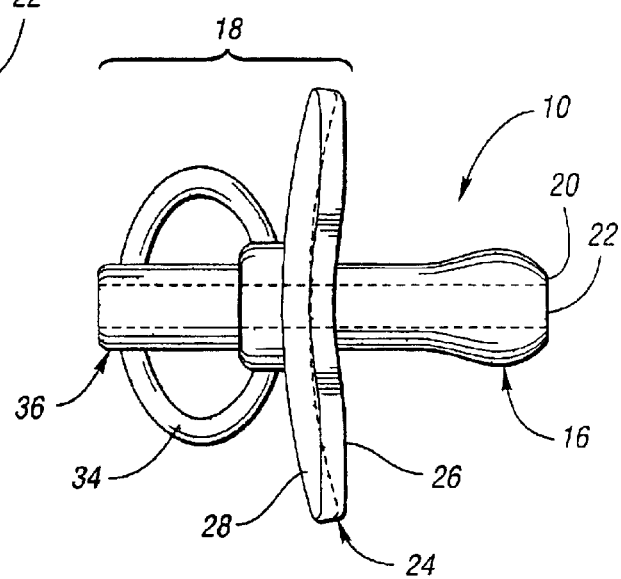
FIG. 2 is a top plan view of the medical pacifier of FIG. 1.
Figure 3:
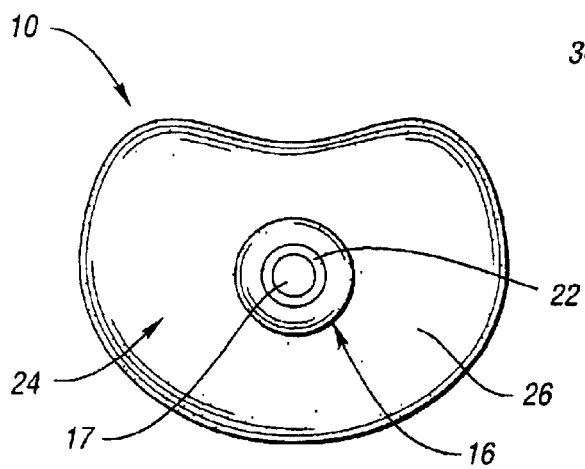
FIG. 3 is a front elevational view of the medical pacifier of FIG. 1.
Figure 4:
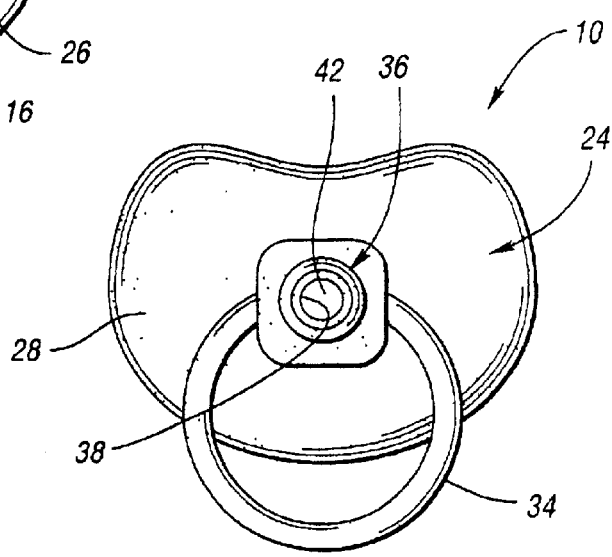
FIG. 4 is a rear elevational view of the medical pacifier of FIG. 1.

The present invention provides a medical pacifier and method of use thereof for delivering anesthesia or other gases to a patient's throat, such that delivery of gases to the lungs is facilitated. Referring to FIGS. 1–6, several views of the medical pacifier of the present invention are shown, wherein the pacifier is designated generally by reference numeral 10. Pacifier 10 includes a nipple member 16 which is intended to be received within a patient's mouth, and a base 18 which is intended to remain outside the patient's mouth.

Nipple member 16 is elongated and generally tubular, although other shapes such as those conforming to the contour of the tongue and/or palate are fully contemplated. Nipple member 16 is hollow, having a conduit 17 extending therethrough, preferably of circular cross-section, that is in communication with an external breathing tube (shown in FIG. 7). At a distal end 20 thereof, nipple member 16 includes an outlet opening 22 of sufficient diameter to allow delivered gas to flow through conduit 17 and into the patient's throat. Although not illustrated, it is understood that a fenestrated distal end 20 of nipple member 16 could be provided as an alternative to opening 22. Furthermore, it is fully contemplated that outlet opening 22 could be provided at any location along nipple member 16. Nipple member 16 also serves to depress the tongue of the pediatric patient, thereby removing an obstruction to the path of the anesthesia gas such that the gas can freely travel to the rearward area of the child's throat where the anesthesia may be inhaled into the lungs, as described below.

Base 18 includes a generally oval-shaped plate 24 that is elongated horizontally and disposed generally perpendicular to the longitudinal axis of nipple member 16. The diameter of plate 24 is sufficiently great so as to inhibit its receipt within the patient's mouth, thereby preventing the patient from choking or swallowing the pacifier 10. Preferably, plate 24 has a concave front surface 26 facing nipple member 16 and an opposed, convex rear surface 28, such that plate 24 is curved to fit the contour of the patient's facial area surrounding the mouth. This configuration provides comfort to the patient as well as providing a good seal when the patient is sucking on nipple member 16. On rear surface 28, plate 24 preferably includes a handle ring 34 pivotally attached thereto which can be grasped by an operator to aid placement of pacifier 10 into the child's mouth.

Referring now to FIGS. 1–2 and 4–6, base 18 further includes a connector 36 projecting from the rear surface 28 of plate 24 in accordance with a preferred embodiment of the present invention. Connector 36 is in the form of a hollow tube, having an outer diameter of approximately 15 mm, wherein an inlet opening 38 is provided at a proximal end 40 thereof. Therefore, base 18 includes a lumen 42 extending therethrough from inlet opening 38 of connector 36 which is in fluid communication with conduit 17 of nipple member 16, as shown in the cross-sectional view of FIG. 6. Connector 36 is adapted to be attached to external tubing as described below with reference to FIG. 7, such that anesthesia or other delivered gases can pass through pacifier 10 and into the patient's throat for inhalation.

Medical pacifier 10 of the present invention is preferably of one-piece construction, molded from a suitable biologically-compatible, hypoallergenic, and structurally durable plastic material, such as polyethylene or polyvinyl chloride (PVC). Alternatively, nipple member 16, base plate 24, and connector 36 can be molded separately, and nipple member 16 and connector 36 secured to base plate 24 using a suitable nontoxic adhesive material. Importantly, nipple member 16 should be constructed from a material that is resilient, while also being strong enough to resist collapsing upon sucking by the child. Pacifier 10 can be constructed to be disposable, or can alternatively be constructed to be sterilized and reused. The overall size of nipple member 16 and base 18 can vary in order to accommodate different age groups of children.

Prior to initiating induction of anesthesia, various medications may be administered to the patient at the discretion of the medical practitioner. Medication may be given prior to the insertion of pacifier 10 into the child's mouth, or alternatively could be impregnated within the plastic material of nipple member 16. In addition, nipple member 16 may be dipped in a dextrose solution to facilitate initial acceptance of the nipple member 16 into the child's mouth.

Once the child has medical pacifier 10 in place in his/her mouth, a standard anesthesia breathing circuit 44 can be quickly and easily attached to connector 36, as shown schematically in FIG. 7, so that induction of anesthesia may begin. Breathing circuit 44 includes an inlet tube 46 which brings anesthesia and other gases toward the patient, and an outlet tube 48 which brings carbon dioxide away from the patient. Some positive pressure, on the order of 2–5 cm $H_2O$, is typically required. First ends 50, 52 of inlet tube 46 and outlet tube 48, respectively, are connected to a source of anesthetic gas, such as a conventional breathing machine 54, the details of which are well known in the art. At the opposite end 56, inlet tube 46 and outlet tube 48 are joined together. Tube end 56 is secured over connector proximal end 40 with an interference fit, ensuring a tight seal to prevent anesthesia gas from escaping at the interface. Alternatively, tube end 56 and connector proximal end 40 could be threaded for mating, or tube end 56 could be formed integrally with pacifier 10. It is contemplated that any suitable commercially available breathing circuit could be utilized with medical pacifier 10 of the present invention.

Therefore, medical pacifier 10 provides a passageway from anesthesia breathing circuit 44 to the patient's oral cavity and throat. As such, once pacifier 10 is connected to breathing circuit 44, the desired concentration of anesthesia and other gases can then be delivered to the patient while the patient is breathing spontaneously. Delivered gas will insufflate the patient's throat and the patient will entrain the gas into each inspired breath, where it will be transported through the trachea to the lungs for entry into the bloodstream.

Medical pacifier 10 of the present invention can be used to achieve an initial level of anesthesia, and thereafter removed and replaced by a standard anesthesia mask (not shown) secured over the child's face for subsequent anesthetizing in the standard fashion. The initial phase of anesthesia is marked by various indicators, such as the loss of an eyelash reflex. Using medical pacifier 10, the initial phase can be complete within 2 to 3 minutes, after which the pacifier 10 can be removed and further anesthetic gases administered by means of the usual face mask without distress to the child.

Alternatively, medical pacifier 10 can be kept in place once the initial level of anesthesia is attained, and a standard face mask can be secured to the patient over the pacifier 10 for subsequent anesthetizing. This alternative method provides the benefit of maintaining an open airway by keeping the tongue away from the roof of the child's mouth.

In addition to the uses described above, medical pacifier 10 of the present invention can also be used to assist with intubation of pediatric patients. Endotracheal tubes are used to ventilate patients for resuscitation, anesthesia, supplying oxygen, and other critical care procedures, and are inserted through a child's mouth for entrance into the respiratory tract. In infants and small children, the voice box may be deeply recessed or otherwise out of view, such that it may be difficult to visualize the vocal cords between which the endotracheal tube must pass for successful intubation. The typical remedy is to numb the upper airway, and insert a fiber optic endoscope 58 and attached camera 59 which can be used to locate the cords. A slightly modified version of medical pacifier 10' of the present invention can aid in this procedure, as illustrated in FIGS. 8 and 9 wherein reference numerals for pacifier 10' correspond to those of preceding figures except for the addition of a prime (') designation. More specifically, endoscope 58 can be inserted through medical pacifier 10' and into the patient's airway while induction of anesthesia proceeds as described above. As shown in FIG. 8, an alternative, generally L-shaped connector 60 is provided, wherein connector 60 is in fluid communication with nipple member 16' and functions as does connector 36 described previously for attachment to breathing circuit 44. In addition, as depicted in FIG. 9, pacifier 10' includes a longitudinal slit 62 formed through nipple member 16', base plate 24', and connector 60. Therefore, endoscope 58 can be inserted into pacifier 10', and then pacifier 10' removed from endoscope 58 via slit 62 once the cords are visualized.

In summary, medical pacifier 10 of the present invention quiets and calms the pediatric patient while providing an adequate oral passageway for efficiently and effectively delivering anesthesia or other gases to a patient. Medical pacifier 10 is familiar in appearance to the infant or child, such that the child tends to relax and retain the pacifier 10 in place and the fear and anxiety associated with standard face masks is substantially eliminated.

Although medical pacifier 10 of the present invention is described herein with reference to induction of anesthesia, it is understood that pacifier 10 can be used to deliver any gases or inhaled-type medications. For example, oxygen alone could be delivered, a combination of oxygen and helium could be delivered for the treatment of asthma, or nebulized medication could be delivered for the treatment of asthma or other conditions. Furthermore, it is also contemplated that pacifier 10 could be modified to provide delivery of gases to the nasal passages in addition to the oral cavity delivery shown and described herein.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A medical pacifier for delivering gas to a patient, the pacifier comprising:
   a nipple member adapted to be received within an oral cavity of the patient, the nipple member having a conduit extending therethrough and a single outlet opening provided in a distal end thereof; and
   a base attached to the nipple member and adapted to remain outside the oral cavity, the base including a generally continuous, annular inlet opening provided therein and a lumen extending therethrough which is in fluid communication with the conduit of the nipple member, wherein the inlet opening has an outer diameter of approximately 15 mm for connecting with a standard breathing tube external to the patient, the breathing tube remaining external to the patient such that gas can flow through the base and the nipple member for delivery via the outlet opening exclusively into the oral cavity of the patient.

2. The medical pacifier according to claim 1, wherein the base includes a base plate disposed generally perpendicular to a longitudinal axis of the nipple member, the base plate having a concave front surface facing the nipple member and a convex rear surface facing away from the nipple member.

3. The medical pacifier according to claim 2, wherein the base further includes a connector projecting from the rear surface of the base plate, wherein the lumen extends through the connector and the inlet opening is disposed in a proximal end of the connector.

4. The medical pacifier according to claim 3, wherein the connector is generally L-shaped.

5. The medical pacifier according to claim 2, further including a handle ring pivotally attached to the rear surface of the base plate.

6. The medical pacifier according to claim 1, wherein the outlet opening is provided in a distal end of the nipple member.

7. The medical pacifier according to claim 1, wherein the nipple member is impregnated with medication.

8. The medical pacifier according to claim 1, wherein the pacifier is molded from a plastic material.

9. The medical pacifier according to claim 1, wherein the pacifier is of one-piece construction.

10. A medical pacifier for delivering anesthetic gas to a patient, the medical pacifier comprising:
a base adapted to remain outside an oral cavity of the patient, the base having a generally concave front surface and a generally convex rear surface;
a generally continuous, annular connector projecting from the base rear surface, the connector including an inlet opening provided in a proximal end thereof and a lumen extending therethrough, the connector proximal end having an outer diameter of approximately 15 mm for receiving a standard breathing tube over the connector proximal end, the breathing tube remaining external to the patient for providing a source of anesthetic gas; and
a nipple member projecting from the base front surface and adapted to be received within an oral cavity of the patient, the nipple member having a conduit extending therethrough which is in fluid communication with the lumen and a single outlet opening provided in a distal end thereof such that anesthetic gas can flow through the pacifier for delivery via the outlet opening exclusively into the oral cavity of the patient.

11. An apparatus for inducing anesthesia in patient, the apparatus comprising:
a breathing circuit including a source of anesthetic gas and an inlet tube connected to the source and operable to transport the gas toward the patient, the inlet tube remaining external to the patient; and
a medical pacifier connected to the breathing circuit, the pacifier including
a nipple member adapted to be received within an oral cavity of the patient, the nipple member having a conduit extending therethrough and a single outlet opening provided in a distal end thereof, and
a base attached to the nipple member and adapted to remain outside the oral cavity, the base including an inlet opening provided therein and a lumen extending therethrough which is in fluid communication with the conduit of the nipple member,
wherein the inlet opening is adapted to be connected to the inlet tube such that anesthetic gas can flow through the base and the nipple member for delivery via the outlet opening exclusively into the oral cavity of the patient.

12. The apparatus according to claim 11, wherein the base includes a base plate disposed generally perpendicular to a longitudinal axis of the nipple member, the base plate having a concave front surface facing the nipple member and a convex rear surface facing away from the nipple member.

13. The apparatus according to claim 12, wherein the base includes a connector projecting from the rear surface of the base plate, wherein the lumen extends through the connector and the inlet opening is disposed in a proximal end of the connector.

14. The apparatus according to claim 13, wherein the proximal end of the connector has an outer diameter of approximately 15 mm.

15. The apparatus according to claim 13, wherein the breathing circuit further includes an outlet tube connected to the source, and the inlet tube and the outlet tube are joined to form a single tube end which is adapted to be fitted over the proximal end of the connector.

16. The apparatus according to claim 13, wherein the connector is generally L-shaped.

17. The apparatus according to claim 12, further including a handle ring pivotally attached to the rear surface of the base plate.

18. The apparatus according to claim 11, wherein pacifier includes a longitudinal slit formed therein for receiving an endoscope.

19. The apparatus according to claim 11, wherein the nipple member is impregnated with medication.

20. The apparatus according to claim 11, wherein the pacifier is molded from a plastic material as a single piece.

21. A method for delivering gas to a patient, the method comprising:
inserting a medical pacifier into an oral cavity of the patient, the pacifier including a nipple member adapted to be received within the oral cavity and having a conduit extending therethrough and an outlet opening provided therein, and a base attached to the nipple member and adapted to remain outside the oral cavity, the base including an inlet opening provided therein and a lumen extending therethrough which is in fluid communication with the conduit of the nipple member;
connecting a gas source to the inlet opening; and
supplying gas through the base and the nipple member for delivery via the outlet opening exclusively into the oral cavity of the patient.

22. The method according to claim 21, wherein supplying gas includes supplying anesthetic gas.

23. The method according to claim 21, wherein supplying gas includes delivering gas toward the pacifier under positive pressure.

24. The method according to claim 21, wherein connecting a gas source includes connecting an external tube to the inlet opening.

25. The method according to claim 21, further including dispensing medication into the oral cavity of the patient via the nipple member.

26. The method according to claim 21, further including dipping the nipple member into a dextrose solution prior to inserting the pacifier into the oral cavity of the patient.

27. The method according to claim 21, further including inserting an endoscope through the pacifier and into the oral cavity of the patient.

28. The method according to claim 21, further including placing a face mask on the patient.

* * * * *